United States Patent [19]

Johnston et al.

[11] Patent Number: 5,026,446
[45] Date of Patent: Jun. 25, 1991

[54] METHOD OF MANUFACTURING A DISPOSABLE DIAPER HAVING AN ABRADED TARGET STRIP

[75] Inventors: Manley R. Johnston, Paris, France; Robert S. Mulder, Eagan; Alan J. Sipinen, Hugo, both of Minn.

[73] Assignee: Minnesota Mining and Manufacturing Company, St. Paul, Minn.

[21] Appl. No.: 361,417

[22] Filed: Jun. 5, 1989

[51] Int. Cl.⁵ .................. A61F 13/60; B32B 31/00
[52] U.S. Cl. .................. 156/153; 51/281 R; 604/389; 604/390; 156/265; 156/256
[58] Field of Search .............. 156/153, 164, 229, 265, 156/256; 604/389, 390; 51/281 R

[56] References Cited

U.S. PATENT DOCUMENTS

| | | |
|---|---|---|
| 2,532,011 | 11/1950 | Dahlquist et al. |
| 2,714,889 | 8/1955 | Chambers .......................... 604/390 |
| 2,958,593 | 11/1960 | Hoover et al. |
| 3,271,229 | 9/1966 | Grabovez . |
| 3,615,992 | 10/1971 | Jeffries et al. |
| 3,951,305 | 9/1976 | Seymour . |
| 4,078,340 | 3/1978 | Klecker et al. |
| 4,237,889 | 12/1980 | Gobran ........................ 604/389 |
| 4,296,750 | 10/1981 | Woon et al. .................... 604/390 |
| 4,436,520 | 3/1984 | Lipko et al. . |
| 4,472,480 | 9/1984 | Olson . |
| 4,530,879 | 7/1985 | Drahnak . |
| 4,544,635 | 10/1985 | Ohashi et al. . |
| 4,710,190 | 12/1987 | Wood et al. ................... 604/390 X |
| 4,813,947 | 3/1989 | Korpman ...................... 604/390 X |
| 4,820,296 | 4/1989 | Masliyah ....................... 604/389 X |
| 4,880,422 | 11/1989 | McBride ........................ 604/389 |

FOREIGN PATENT DOCUMENTS 2129689  5/1984  United Kingdom ............... 604/389

OTHER PUBLICATIONS

Shields, J., *Adhesives Handbook*, CRC Press, 1970, pp. 235-236 and 244-250.

Primary Examiner—Michael W. Ball
Assistant Examiner—Jeff H. Aftergut
Attorney, Agent, or Firm—Gary L. Griswold; Roger R. Tamte; William J. Bond

[57] ABSTRACT

In the continuous manufacture of disposable diapers wherein target strips applied to the diaper are cut from a pressure-sensitive adhesive tape that has a low-adhesion backsize coating, better adhesion of adhesive closure tabs to the target strips is obtained after physically abrading the low-adhesion backsize coating. A preferred abrading medium is a low density open nonwoven fibrous abrasive web.

8 Claims, 1 Drawing Sheet

METHOD OF MANUFACTURING A DISPOSABLE DIAPER HAVING AN ABRADED TARGET STRIP

BACKGROUND OF THE INVENTION

1. Field of the Invention

The invention concerns a disposable diaper, specifically one having a target strip for a pair of adhesive closure tabs. In particular, the invention concerns the manufacture of the target strip.

2. Description of the Related Art

Disposable diapers typically have an outer shell of thin plastic film such as polyethylene, which is reinforced at the areas where adhesive closure tabs are adhered during fastening of the diaper around a wearer. The reinforcement frequently is a stronger plastic film that is adhesively attached to the outer shell and is often called a "target strip". A typical method of continuously making and applying the target strip includes the steps of: a) unwinding a roll of pressure-sensitive adhesive tape having a backing such as biaxially oriented polypropylene ("BOPP") film that has a low-adhesion backsize coating on its nonadhesive face, b) cutting the tape into pieces, and c) adhering one piece of the tape by its pressure-sensitive adhesive layer to the outer shell of each diaper to provide a target strip. While the low-adhesion backsize coating permits the tape to be unwound from the roll, it has a deleterious effect on adhesion of the adhesive closure tabs to the target strip. Although this problem can be avoided by employing a release liner instead of a low-adhesion backsize coating, doing so would be more expensive.

The problem of poor adhesion of the closure tabs to a low-adhesion backsize coating can also be avoided by coating the adhesive onto the backing film of the target strip on-line with the diaper-making operation. However, at the high speeds used in diaper-making lines, this results in an adhesive coating that may be undesirably uneven in thickness and may deviate excessively from the edges of the film.

3. Other Prior Art

U.S. Pat. No. 3,165,992 (Jeffries) concerns film adhesives that may or may not be normally tacky and typically are wound up with a double-coated release paper. Jeffries concerns the problem that after the adhesive film has been unwound and applied to an object, the release paper can be difficult to remove. Jeffries solves this problem by abrading away at least part of the release coating at one face of the release paper, thus permitting easy removal of the release paper by applying a pressure-sensitive adhesive tape to the abraded surface.

U.S. Pat. No. 3,271,229 (Grabovez) physically abrades the surface of a thermoplastic film such as poly(ethylene terephthalate) or polypropylene to provide improved slip, i.e., lower friction; the abrasion is accomplished with a brush having non-metallic bristles or fibers. U.S. Pat. No. 2,951,305 (Seymour) physically abrades poly(ethylene terephthalate) film with a wire brush in order to dull its surface appearance. Neither Grabovez or Seymour suggests that the surface being abraded might have first received any sort of coating.

SUMMARY OF THE INVENTION

The invention provides an economical method for continuously furnishing disposable diapers with target strips to which adhesive closure tabs reliably adhere. The novel method includes the above-outlined steps of continuously making and applying a target strip and so employs a roll of tape, the backing of which has a low-adhesion backsize coating.

The novel method differs from the above-outlined method by adding the step of physically abrading the low-adhesion backsize coating while the tape is being unwound to provide target strips to which adhesive closure tabs adhere more reliably.

In order to enhance handling of the tape while it is being abraded, the abrading step should be carried out prior to the step of cutting the tape into pieces. Also prior to the cutting step, there preferably is a second added step of cleaning off any debris formed in the abrading step, thus preventing the debris from interfering with a good adhesion between the adhesive closure tabs and the target strips.

The novel method provides additional advantages. For example, the abraded target strips have a matte appearance that imparts an aura of high quality to the diapers, in contrast to the shiny, and hence artificial, appearance of target strips of most disposable diapers now on the market. Such a benefit can exist irrespective of whether a low-adhesion backsize is present on the target strip, and the invention applies to such products. Furthermore, in a diaper of the invention, the adhesive closure tabs peel back smoothly from the target strip, whereas they tend to have shocky peelback from prior target strips that have low-adhesion backsize coatings. Consumers are likely to equate a smoother peelback with higher quality.

Useful materials for the target strips are those currently employed in the manufacture of target strips for diapers, e.g., high-strength thermoplastic films such as biaxially oriented polypropylene film or biaxially oriented poly(ethylene terephthalate) film, preferably having thicknesses from 15 to 40 $\mu$m. Backings that are biodegradable or otherwise environmentally degradable, e.g., cellophane, also have value.

Preferred low-adhesion backsize coatings include urethane backsizes as described in U.S. Pat. No. 2,532,011 (e.g. made by reacting octadecyl isocyanate with a polymer of vinyl alcohol), fluorochemical backsizes (such as fluorochemical acrylates described in U.S. Pat. No. 4,472,480), ultraviolet-light curable silicone backsizes described in U.S Pat. No. 4,530,879, and thermally curable backsizes described in U.S Pat. No. 4,544,635. The thickness of the low-adhesion backsize coating typically is from 0.1 to 1 $\mu$m, and it is presently contemplated that at least 10 percent of the low-adhesion backsize coating be desirably removed in the abrading step of the novel method, more preferably at least 20%. The low-adhesion backsize may be completely removed, but it is difficult to accomplish that economically and without slowing the rate at which the disposable diapers are being produced.

DETAILED DESCRIPTION OF THE INVENTION

While the present invention can employ any of a variety of abrading tools or materials, a preferred abrading material is a low-density open nonwoven fibrous abrasive web such as is commercially available under the trademark Scotch-Brite ® from the 3M Company to which this application is assigned. That abrasive web is supplied in various useful conformations such as small pads, larger sheets, discs, brushes, wheels, and rolls and is described in U.S. Pat. No. 2,958,593 (Hoover) which is incorporated herein by reference. In general, the abrasive webs are formed from randomly disposed fibers, e.g., polyesters, polyamides, nylons and rayons, which are bonded at points where they intersect to provide a three-dimensional structure; and abrasive particles are bonded to the fibers with a binder. See also, U.S. Pat. No. 4,078,340 (Klecker et al.) which is incorporated herein by reference.

Other techniques for physically abrading away at least part of the low-adhesion surface include abrasion with materials such as sandpaper and wire brushes.

The amount of material to be abraded away when using a "Scotch-Brite" low-density abrasive web can be controlled by varying a number of parameters, e.g. the fineness of its fibers, the firmness and thickness of the web, the type and loading of its abrasive particles, and the density of the web. The abrasive action of the abrasive web can also be varied in a number of ways, e.g. the speed of the web or the tape being abraded can be varied, the abrasive web can either be oscillated or held steady, the oscillation speed can be varied, the stroke distance can be varied, and the applied pressure of the abrasive web can be adjusted. Typically, a tape while being abraded is supported by a backup roll or belt which can either be smooth or patterned, e.g., a raised diamond pattern that can be chosen to cause abrasion in the patterned areas. Abrasion can be caused in a selected fraction of the area of the low-adhesion backsize coating to provide a desired degree of adhesion of adhesive closure tabs.

The action of the nonwoven abrasive web can be in only one direction or in multiple directions, e.g., first in the cross-web direction and, then in the down-web direction to provide a cross-hatched texture. Abrading techniques that are fastest and hence the most economical tend to create fine parallel grooves in the backsized surface of the target strip that afford an aesthetically pleasing matte appearance.

Debris loosened by the abrading step can be removed in various ways such as vacuuming or blowing air or by wiping with a blade, pad or brush, or by washing with water. Preferably an air knife is used to loosen the debris, and a vacuum box collects the debris. In some cases it may be desirable to use water in a washing or wiping process to clean the film produced.

Figure 1:
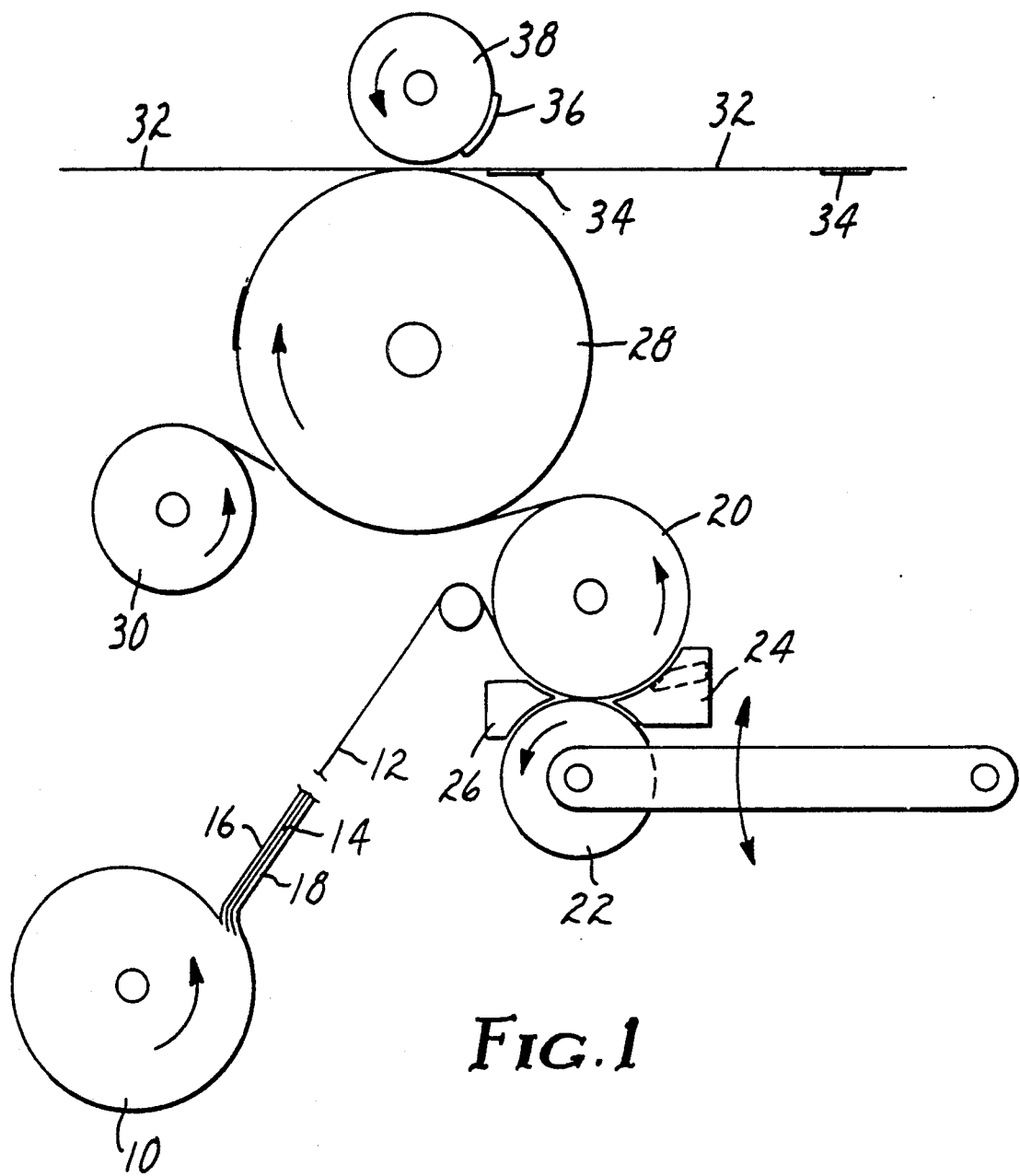
FIG. 1 is a schematic representation of an apparatus suitable for inclusion in equipment for the continuous manufacture of disposable diapers, which apparatus abrades and applies a target strip to each diaper.

The apparatus of FIG. 1 employs a roll 10 of pressure-sensitive adhesive tape 12 that has a backing 14 of high-strength thermoplastic film bearing a pressure-sensitive adhesive layer 16 and a low adhesion backsize coating 18. The tape 12 is carried into the nip between a metal roll 20 that has a release surface and a counter-rotating abrasive brush 22, specifically a Scotch-Brite ® brand cleaning and finishing brush. This abrades away at least part of the low-adhesion backsize coating 18.

As the tape 12 leaves the nip, it passes beneath an air-knife vacuum manifold 24 to clean, off debris, while another vacuum manifold 26 removes debris from the abrasive brush 22 as it rotates away from the nip. The tape 12 is then fed onto a vacuum wheel 28 at which a rotary cutter 30 cuts it into pieces, each of which is adhered by the pressure-sensitive adhesive layer 16 to a diaper web 32 as an individual target strip 34, pressure being applied by a rubber pad 36 on a steel roll 38.

Figure 2:
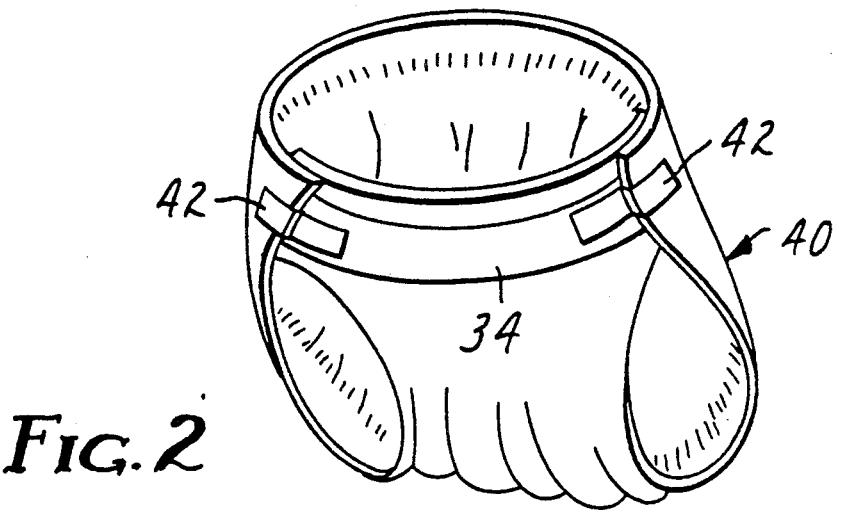
FIG. 2 schematically shows a disposable diaper to which a target strip has been applied as shown in FIG. 1.

A disposable diaper 40 which bears one of the target strips 34 and a pair of adhesive closure tabs 42 is shown in FIG. 2.

135° PEEL ADHESION TEST

This test employs a pressure-sensitive adhesive fastening tape, the backing of which is a polypropylene film (0.1 mm in thickness) having a matte finish on each surface (made by extruding Dypro 8771 resin available from Fina Oil and Chemical Co., colored white with 5% by weight of a blend comprising 50 weight percent each of titanium oxide and polypropylene) and bearing a pressure-sensitive adhesive layer that was coated from a solution of 45.45 parts "Kraton" 1107 elastomer (from Shell Chemical Co.), 9.09 parts mineral oil, and 45.45 parts by weight "Wingtack" 95 tackifier (from Goodyear Chemical Co.) and as dried, has a coating weight of 33.5 g/m$^2$. "Kraton" 1107 elastomer is a styrene-isoprene-styrene block copolymer, 14% styrene, having a melt index, Cond. G, of 9.

A piece of target strip to be tested is adhered by a double-coated pressure-sensitive adhesive tape to cover a 2 inch×5 inch×1/16 inch (5.08 cm×12.7 cm×0.16 cm) smooth steel panel, with the lengthwise direction of the target strip extending in the length of the panel. A one-inch (2.54-cm) wide piece of the fastening tape is centered on the target strip and immediately rolled lengthwise, one pass in each direction, with a mechanically operated 4.5-pound (2.04-kg) roller. A peel test is carried out at constant temperature (23°±2° C.) and humidity (50±2% relative humidity) using a constant-rate-extension Instron tensile tester (model 1122). Within 15 seconds after the fastening tape is rolled on the target strip, a leader of the fastening tape is clamped into the upper jaw of the tensile tester, and the crosshead peels the fastening tape at an angle of 135° at 12 inches/minute (30.5 cm/minute). The peel value is read from the chart, disregarding the portion of trace due to the initial and final ¼ inch (0.635 cm) of the tape removed. The measurement is replicated at least twice and averaged.

At from 1 to 3 N/cm of width in this 135° Peel Adhesion Test, a target strip should provide the most reliable and conveniently usable closure for a disposable diaper. A value substantially below this range would indicate unreliable closure, or substantially above this range would indicate that some persons might have difficulty in peeling closure tabs from the target strip. However, for some uses, higher adhesion values are desirable.

ROUGHNESS TESTING

In order to evaluate the roughness of abraded films of the invention, a technique described generally in U.S. Pat. No. 4,436,520 (Lipko) was used with a Surtronic 3 profilometer (from Taylor-Hobson, Leicester, U.K.). Using a stylus 5 μm in radius, the abraded surface was evaluated for Ra and Peak Count wherein Ra is the arithmetical mean deviation of the profile in μm and Peak Count is the number of peaks per cm using a bandwidth of zero.

60° GLOSS VALUE

This was measured with a 60° "Glossgard" II glossmeter (from Gardner Co., Bethesda, Md.).

The following Examples are in parts by weight and are provided to illustrate the invention but not to limit it.

EXAMPLE 1

A film of 10-inch (25.4-cm) width biaxially-oriented polypropylene was hot melt coated on one surface with 4 grains (17 g/m$^2$) of adhesive formulated as 50% "Kraton" 1107 elastomer, 49% "Wingtack Plus" tackifier, and 1% "Irganox" 1076 (available from Ciba-Geigy Corp., Ardsley, N.Y.). The other surface of the resulting tape was coated with a 5% solution in xylene/heptane/isopropyl alcohol of urethane-low adhesion backsize (0.19 g/m$^2$ dry weight) prepared from octadecyl isocyanate and polyvinyl alcohol per U.S. Pat. No. 2,532,011.

Using a Scotch-Brite® brand No. 96 general purpose scouring pad, the dried low-adhesion backsize coating was lightly abraded by hand for about 30 seconds in one direction and then 30 seconds in a direction perpendicular to the first until the glossy nature of the surface was modified to provide a texturized surface having a matte appearance. The texturized surface was then lightly wiped to remove most of the debris. In the 135° Peel Adhesion Test (using the fastening tape described below), the force to remove a fastening tape from the abraded surface was 6.75 N/cm, and to remove the fastening tape from an identical backsized film which had not been abraded, 0.66 N/cm. In this test, the backing of the fastening tape was a 5.0 mil (0.13 mm) embossed polypropylene film (made by extruding Dypro 8771 resin available from Fina Oil and Chemical, Dallas, Tex., colored white with 5% by weight of 50/50 titanium dioxide in polypropylene), and the pressure-sensitive adhesive layer (50 g/m$^2$) consisted of 33% Kraton 1107 (available from Shell Chemical Co ), 46.9% Escorez 1310 (available from Exxon Chemical Co.) 19.1% Zonarez A-25 (available from Arizona Chemical Co.), and 1.0%, Irganox 1076 antioxidant. The fastening tape peeled smoothly from the abraded film, whereas the unabraded film produced a shocky peel.

EXAMPLE 2

A pressure-sensitive adhesive tape as described in the first paragraph of Example 1 was unwound at a linespeed of 40 feet (12.2 meter) per minute and passed through the nip between a metal roll and a Scotch-Brite® Cleaning and Finishing Brush Type 5S, ultrafine grade, about 8 inches (20 cm) in diameter, there being a 2 kg pressure at the nip. The rotation of the brush was in the same direction as the movement of the tape and at speeds in steps from 200 to 1000 feet (61 m to 305 m) per minute. Test results are in Table I together with the "Control" test result reported in Example 1.

TABLE I

| Brush Speed | | 135° Peel Adhesion Test* |
|---|---|---|
| (fpm) | (m/min) | (N/cm of width) |
| 200 | 61 | 5.0 smooth |
| 400 | 122 | 5.6 smooth |
| 600 | 183 | 5.2 smooth |
| 800 | 244 | 5.0 smooth |
| 1000 | 306 | 6.2 smooth |
| Control | | 0.7 shocky |

*Using the fastening tape of Example 1

EXAMPLES 3–21

Used in these examples was 1.0 mil (0.0254 mm) biaxially oriented polypropylene film [B502 (BOPP) available from Hercules Chemical] that had been coated with a 5% solution of the urethane low-adhesion backsize (0.19 g/m$^2$) described in Example 1. A 3-foot (39-cm) length of the film was taped at its edges to a rigid metal panel with its low-adhesion backsize coating facing outwardly. The panel was then pushed by hand through a nip between a rubber-covered roll and a counter-rotating Scotch-Brite® brand cleaning and finishing brush about 8 inches (20.3 cm) in diameter. In doing so, the panel was transported at the peripheral speed of the rubber-covered roll (9 m/min.). The various Scotch-Brite® cleaning and finishing brushes were used as indicated in Table II, namely, 7S Superfine, 5A Very Fine, and 7A Fine. Table II indicates brush roll speed and brush pressure and reports the results of peel adhesion, roughness and gloss testing of the abraded surfaces of the films of Examples 3–21. For comparative purposes, some of the films of Examples 3–21 had no low-adhesion backsize coating. Results for Examples 24C, described below, are included as another comparison.

TABLE II

| Example No. | Backsize Present | Brush Type | Brush Speed (RPM) | Relative Brush Pressure | 135° Peel Adhesion (N/cm) | Roughness Ra | Peak Count | 60° Gloss |
|---|---|---|---|---|---|---|---|---|
| 3 | Yes | 7S | 600 | Low | 2.0 | 0.25 | 16 | — |
| 4 | Yes | " | 1200 | Low | 2.1 | 0.28 | 33 | 46 |
| 5 | Yes | " | 1200 | High | 2.4 | 0.28 | 59 | 23 |
| 6 | Yes | " | 1800 | High | 2.6 | 0.43 | 77 | — |
| 7 | Yes | " | 1800 | Low | 2.1 | 0.30 | 15 | 34 |
| 8 | Yes | " | 600 | High | 2.4 | 0.46 | 21 | 31 |
| 9 | No | " | 1800 | High | 2.5 | 0.43 | 61 | 23 |
| 10 | Yes | 5A | 1200 | Low | 1.5 | 0.36 | 11 | 74 |
| 11 | Yes | " | 600 | High | 1.9 | 0.41 | 28 | 55 |
| 12 | Yes | " | 600 | Low | 1.5 | 0.28 | 17 | 81 |
| 13 | Yes | " | 1200 | High | 2.1 | 0.69 | 45 | 27 |
| 14 | Yes | " | 1800 | Low | 1.6 | 0.20 | 8 | — |
| 15 | No | " | 1800 | High | 2.7 | 0.56 | 18 | 39 |
| 16 | Yes | 7A | 1200 | Low | 1.5 | 0.28 | 14 | — |
| 17 | Yes | " | 1200 | High | 1.9 | 0.64 | 33 | 28 |
| 18 | Yes | " | 600 | High | 1.7 | 0.76 | 14 | 70 |

TABLE II-continued

| Example No. | Backsize Present | Brush Type | Brush Speed (RPM) | Relative Brush Pressure | 135° Peel Adhesion (N/cm) | Roughness Ra | Peak Count | 60° Gloss |
| --- | --- | --- | --- | --- | --- | --- | --- | --- |
| 19 | Yes | " | 600 | Low | 1.5 | 0.33 | 15 | 96 |
| 20 | Yes | " | 1800 | Low | 1.6 | 0.28 | 19 | 97 |
| 21 | Yes | " | 1800 | High | 2.1 | 0.41 | 43 | 40 |
| 24C | Yes | — | — | — | 0.86 | 0.17 | 9 | 134 |

EXAMPLE 22

A 2.2 mil (0.0559 mm) clear matte cast film made by extruding WRS-7-319, a resin consisting of polypropylene/polyethylene copolymer [available from Shell Chemical Co.], was coated with a 5% solution of the urethane low-adhesion backsize (0.38 g/m²) described in Example 1. This low-adhesion backsize coating was abraded in the same way as in Example 14 except that the brush was rotated in the same direction as the rubber-covered roll. Testing is reported in Table III together with two controls of which Example 22-C was an identical tape that was not abraded, and Example 22-CC was an abraded identical tape except having no low-adhesion backsize coating.

TABLE III

| Example No. | 135° Peel Adhesion | Roughness Ra | Peak Count |
| --- | --- | --- | --- |
| 22 | 2.0 | 1.27 | 101 |
| 22-C | 1.2 | — | — |
| 22-CC | 2.6 | 0.91 | 122 |

EXAMPLE 23

Used to make target strips was a roll of 10-inch width (25.4-cm) biaxially oriented polypropylene film (BOPP) bearing on one surface a pressure-sensitive adhesive and on the other surface a coating with 5% by weight of urethane low-adhesion backsize (0.19 g/m²) as in Example 1. While being unwound at a linespeed of 100 feet per minute (30.5 m/min.), this tape was passed between a rotating idler roll and an abrading brush (Scotch-Brite ® 5A fine cleaning and finishing brush) of about 8 inches (20.3 cm) in diameter and 10 inches (25.4 cm) in width that was counter rotated at a 3.25 rpm dial setting. The roll pressure was maintained at 50 psi (34 N/cm²). The generated debris was then removed by a combination vacuum and air knife. Static eliminators were also mounted in the line immediately above the abrading brush. Test results are shown in Table IV, which also reports the residual amount of urethane backsize after abrasion, determined by infrared spectroscopic measurements that compare the urethane absorption present before and after abrasion. Also reported in Table IV as Example 23-C (a control) is testing of an identical tape that was not abraded.

EXAMPLES 24-25

Example 23 was repeated except using BOPP that had no adhesive coating and using a different rpm of the abrading brush as indicated in Table IV. Also reported in Table III as Example 24-C is an unabraded control.

TABLE IV

| Example No. | Linespeed (m/min) | RPM Setting | Residual Urethane Level on Surface | 135° Peel Adhesion Test (N/cm) |
| --- | --- | --- | --- | --- |
| 23 | 30.5 | 3.25 | 34% | 1.5 |
| 24 | 30.5 | 9 | 88% | 1.7 |
| 25 | 30.5 | 3.25 | 14% | 1.8 |
| 23-C | — | — | 100% | 1.1 |
| 24-C | — | — | 100% | 0.86 |

As noted above, the matte appearance afforded by abrading the surface of a thermoplastic film imparts an aura of quality as compared to unabraded film. For this reason, it may be desirable for the target strip of a diaper to have an abraded surface, whether or not the surface being abraded originally carried a low-adhesion backsize coating. Furthermore, the degree of adhesion of a diaper closure tab to a target strip changes when the exposed surface of the target strip is abraded, whether or not a low-adhesion backsize coating had previously been applied to that surface or was applied after it had been abraded. These and other facets of the invention will occur to one skilled in the art.

What is claimed is:

1. In a method of continuously manufacturing disposable diapers, which method includes the steps of unwinding a roll of pressure-sensitive adhesive tape which has a backing having a thickness of less than about 40 μm that bears a low-adhesion backsize coating on its nonadhesive face, cutting the tape into pieces, and adhering at least one piece of the tape by its pressure-sensitive adhesive layer to each diaper to provide a target strip, said method being characterized by the added step of treating the tape with an abrasive surface so as to remove at least part, but not all, of the low-adhesion backsize coating on the backing with the abrasive surface having a grit size which will so remove only a portion of the backsize coating to improve peel adhesion thereof to pressure-sensitive adhesive tape.

2. Method as defined in claim 1 wherein the abrading step is carried out before the step of cutting the tape into pieces.

3. Method as defined in claim 1 and further comprising the step of cleaning from the abraded face of the tape debris created in the abrading step.

4. Method as defined in claim 1 wherein sufficient material is removed in the abrading step so that the abraded surface of the target strip has a matte appearance.

5. Method as defined in claim 4 wherein said backing is a thermoplastic film.

6. Method as defined in claim 1, wherein the abrading step abrades the low-adhesion backsize coating in a pattern of areas to provide a preselected degree of adhesion of adhesive closure tabs.

7. Method as defined in claim 6 wherein said pattern is a diamond pattern.

8. Method of continuously manufacturing disposable diapers, which method comprises the steps of
   a) providing a roll of pressure-sensitive adhesive tape comprising a backing less than about 40 μm thick bearing a pressure-sensitive adhesive layer and low-adhesion backsize coating covering the nonadhesive face of the film,
   b) unwinding the tape,
   c) treating the low-adhesion face of the backing with an abrasive surface to remove at least part, but not all, of the low-adhesion backsize coating with the surface of having a grit size which will so remove only a portion of the backsize coating to provide a matte finish thereon with improved peel adhesion to pressure-sensitive adhesive tape,
   d) cutting the tape into pieces,
   e) adhering one piece of the tape to each diaper to provide a target strip.

* * * * *

UNITED STATES PATENT AND TRADEMARK OFFICE
CERTIFICATE OF CORRECTION

PATENT NO. : 5,026,446
DATED : June 25, 1991
INVENTOR(S) : JOHNSTON ET AL.

It is certified that error appears in the above-identified patent and that said Letters Patent is hereby corrected as shown below:

Column 1, line 42, delete "3,165,992" and insert therefor —3,615,992—.

Column 3, line 66, delete "clean," and insert therefor —clean—.

Signed and Sealed this

Twenty-fourth Day of November, 1992

Attest:

DOUGLAS B. COMER

*Attesting Officer*     *Acting Commissioner of Patents and Trademarks*